US010813829B2

(12) United States Patent
Liyanage et al.

(10) Patent No.: US 10,813,829 B2
(45) Date of Patent: Oct. 27, 2020

(54) SMART MATERIAL BASED PENILE STIMULATION ERECTILE DYSFUNCTION ASSISTANCE DEVICE

(71) Applicants: CIRQ MATERIALS LIMITED, Tsimshatsui, Kowloon, Hong Kong (CN); Biman Najika Liyanage, Battaramulla (LK); Mitchell Martin Miller, Dana Point, CA (US); Alexander Ververis, Emmendingen (DE)

(72) Inventors: Biman Najika Liyanage, Battaramulla (LK); Mitchell Martin Miller, Dana Point, CA (US); Alexander Ververis, Emmendingen (DE)

(73) Assignee: CIRQ TECHNOLOGIES LIMITED, Kowloon (HK)

(*) Notice: Subject to any disclaimer, the term of this patent is extended or adjusted under 35 U.S.C. 154(b) by 132 days.

(21) Appl. No.: 15/779,032

(22) PCT Filed: Dec. 16, 2015

(86) PCT No.: PCT/CN2015/097608
§ 371 (c)(1),
(2) Date: May 24, 2018

(87) PCT Pub. No.: WO2017/088217
PCT Pub. Date: Jun. 1, 2017

(65) Prior Publication Data
US 2018/0353372 A1    Dec. 13, 2018

(30) Foreign Application Priority Data
Nov. 25, 2015    (CN) .................... 2015 2 0951241 U

(51) Int. Cl.
*A61F 5/41*    (2006.01)
*A61H 19/00*    (2006.01)
(Continued)

(52) U.S. Cl.
CPC ............. *A61H 19/32* (2013.01); *A61B 5/026* (2013.01); *A61B 5/4393* (2013.01); *A61F 5/41* (2013.01);
(Continued)

(58) Field of Classification Search
CPC ............ A61B 8/06; A61B 5/11; A61B 5/4393
(Continued)

(56) References Cited

U.S. PATENT DOCUMENTS 4,913,162 A  *  4/1990  Leang ................. A61B 5/4393
                                                              33/512
5,692,520 A     12/1997  Lavoisier
(Continued)

FOREIGN PATENT DOCUMENTS

| CN | 104545828 A | 4/2015 |
| CN | 104665820   | 6/2015 |

(Continued)

OTHER PUBLICATIONS

Office Action and Search Report dated Nov. 1, 2019 issued by China Intellectual Property Office for counterpart 201580084827.8.
(Continued)

*Primary Examiner* — Samuel G Gilbert
(74) *Attorney, Agent, or Firm* — WPAT, P.C., Intellectual Property Attorneys; Anthony King

(57) ABSTRACT

This invention will allow men suffering from full and periodic erectile dysfunction to achieve, or at least assist in the process of achieving a firm and lasting erection. And, for all men, this device will be able to measure blood-flow to the penis, as well as increase sexual pleasure through micro-
(Continued)

electronic stimulation to the penis (induce erection). Blood-flow data captured from devices' internal sensors will be processed by software and presented to users via a smartphone app to provide useful, actionable, and customizable tasks to improve penile and overall sexual performance, health, and wellness.

11 Claims, 1 Drawing Sheet

(51) Int. Cl.
    *A61B 5/026*     (2006.01)
    *A61B 5/00*     (2006.01)
    *A61F 6/04*     (2006.01)

(52) U.S. Cl.
    CPC .......... *A61F 6/04* (2013.01); *A61F 2005/414* (2013.01); *A61F 2005/417* (2013.01); *A61F 2005/418* (2013.01); *A61H 2201/02* (2013.01); *A61H 2201/10* (2013.01); *A61H 2201/1207* (2013.01); *A61H 2201/169* (2013.01); *A61H 2201/5043* (2013.01); *A61H 2201/5079* (2013.01); *A61H 2201/5082* (2013.01); *A61H 2201/5097* (2013.01); *A61H 2230/255* (2013.01)

(58) Field of Classification Search
    USPC ........................................... 600/38, 507, 587
    See application file for complete search history.

(56) References Cited

U.S. PATENT DOCUMENTS

| | | | |
|---|---|---|---|
| 6,251,076 B1* | 6/2001 | Hovland | ............. A61B 5/4393 600/454 |
| 6,814,695 B1 | 11/2004 | Wyllie et al. | |
| 2005/0195118 A1 | 9/2005 | Ito et al. | |
| 2007/0049792 A1 | 3/2007 | Levy | |
| 2011/0295156 A1 | 12/2011 | Krturi | |
| 2012/0172661 A1 | 7/2012 | Chiu | |
| 2014/0171767 A1* | 6/2014 | Hotaling | .................. A61B 8/06 600/323 |
| 2016/0290880 A1* | 10/2016 | Lewis | .................. G01L 1/2287 |

FOREIGN PATENT DOCUMENTS

| | | |
|---|---|---|
| DE | 10022336 A1 | 11/2001 |
| EP | 1790381 A1 | 5/2007 |
| JP | 2006-51105 A | 2/2006 |
| WO | WO92/09962 A1 | 6/1992 |
| WO | NO 2004028361 A1 | 4/2004 |
| WO | WO 2012176111 A2 | 12/2012 |
| WO | WO 2012176111 A3 | 12/2012 |
| WO | WO2014/147584 A1 | 9/2014 |

OTHER PUBLICATIONS

English summary of the Office Action and Search Report dated Nov. 1, 2019 issued by China Intellectual Property Office for counterpart 201580084827.8.

Office Action and Search Report dated Apr. 17, 2020 issued by European Patent Office for counterpart application No. 15909128.9.

Office Action and Search Report dated Jun. 24, 2020 issued by China National Intellectual Property Administration for counterpart application 201580084827.8.

English Abstract Translation of Office Action issued by China National Intellectual Property Administration.

* cited by examiner

SMART MATERIAL BASED PENILE STIMULATION ERECTILE DYSFUNCTION ASSISTANCE DEVICE

TECHNICAL FIELD

The present invention relates to an electric penile ring, particularly a penile ring that can measure the blood-flow, recognize the flow pattern based on the data model, and/or accelerate blood-flow of the penis.

BACKGROUND ART

Sexual health, well-being, and sexual pleasure are all important aspects to the lives of healthy adults. For men, the foundation of sexual activity and sexual pleasure is the ability to achieve and sustain a firm erection, for the purpose of sexual intercourse and/or sexual play.

There are 3 main product categories related to sexual pleasure and male erectile dysfunction in the market: pleasure products, diagnostic/measurement devices, and stimulation devices.

Pleasure Products: there are a variety of pleasure products and similar devices designed to enhance user's erotic stimulation when applied to erogenous zones. There are a wide variety of condoms used for safer sex as well as increased pleasure through various textures, colors, thickness, shapes, etc. . . . . Penile Constrictive Devices can be used with or without a condom, and also come in a wide variety of forms. There are rigid cock rings made of metals and plastics, as well as stretchable versions made from silicon and other rubbers. Some also include vibrating mechanisms, batteries, and penis thrust "pedometers", that measure simple back and forth motions.

Pleasure products available in the market today, may or may not increase users' pleasure or sexual performance, nor are they able to take accurate measurements or specifically assist with erectile dysfunction.

Diagnostic/Measurement:

Sphygmomanometer cuff can be applied to an erect penis to measure penile blood pressure;

Plethysmograph: This device comprises a loop-shaped silicone elastomer tubing filled with mercury. The tubing is positioned around the penis of the patient and is connected to an electrical circuit; used to measure penile circumference change due to penile erection;

Measurement of NPT is usually performed with the help of a Plethysmograph. This device comprises loop-shaped silicone elastomer tubing filled with mercury. The tubing is positioned around the penis of the patient and is connected to an electrical circuit. Any change in the circumference of the penis causes stretching of the silicone tubing which in turn triggers a variation in the electrical resistance of the mercury filling. The electrical circuit will measure this change in resistance which can then be translated into a measure of the increase in penile circumference. This measurement allows one to determine penile tumescence.

U.S. Pat. No. 5,692,520 A recorded "The present invention is directed to a non-invasive method and apparatus for measuring arterial and venous blood flow in body appendages. The present invention is also directed to a non-invasive method and apparatus for measuring penile tumescence as a function of arterial and venous blood flow in the penis and penile rigidity as a function of suprasystolic intra-cavernosal pressure. These measurements are performed to make a diagnosis in the field of erectile dysfunctions".

Stimulation Device: Flextronics Viberect

Viberect is an electronic, clamp-like device that delivers vibratory stimulation to both surfaces of the penis (dorsal and ventral) to induce erection and ejaculation. The product claims to assist men with mild to moderate erectile dysfunction, men recovering from pelvic surgery, and/or men who have suffered spinal cord injury to obtain erection and/or ejaculation. Current diagnostic and penile stimulating devices, are often physically wired to larger machines, are complicated, require the assistance of trained professionals, and/or are too large and bulky to actually be used and take measurements during sexual intercourse.

In order to promote sexual safety and improve erectile dysfunction, the Center for Disease Control (CDC) of the Department of Health advocates the use of condoms and/or vibrating mechanisms; these measures produce minimal result. The inventor has therefore developed the Smart Material Based Penile Stimulation Erectile Dysfunction Assistance Device to provide people with safe and effective alternative to products currently on the market.

SUMMARY OF THE INVENTION

An object of the present invention is to provide Smart Material Based Penile Stimulation Erectile Dysfunction Assistance Device to assist with achieving or maintaining an erection.

The primary objective of the present invention is Smart Material Based Penile Stimulation Erectile Dysfunction Assistance Device comprises the following layers:
  actuation or stimulation part; and/or
  data transmission layer; and/or
  measurement sensor layer that measures circumferential elongation and/or doppler blood-flow and blood-flow change;
  wherein said measurement sensor layer is powered with power means;
  preferably, the said layers are in radial order from the inside to the outside.

In a further embodiment, the said measurement sensor layer further comprises a measurement sensor designed to measure temperature.

In a further embodiment, wherein power means comprise Wi-Fi powered internal flexible battery, internal lithium-ion rechargeable battery, internal lithium-ion disposable battery, internal disposable "coin" battery, and/or liquid ion battery.

In a further embodiment, the said actuation or stimulation part comprises one or more actuation or stimulation modes selected from electrical-mechanical stimulation, electrical point stimulation, smart material "contraction" actuation, electrical micro-vibration or temperature stimulation, and/or texture stimulation.

In a further embodiment, further comprising a data display member.

In a further embodiment, the said data display member is shown by means of colored lights, LCD display, LED display, and/or flexible-printable display.

In a further embodiment, the said data transmission layer transmits data through Bluetooth, NFC, RFID and/or Wi-Fi.

In a further embodiment, smart material further comprises silicon, shape memory alloy, advanced piezo composites, and/or macro fiber composites.

In a further embodiment, SMBPSEDAD is used with or without a condom.

To enable a further understanding of the aforesaid objectives and the technological methods of the invention herein, the brief description of the drawings below is followed by the detailed description of the preferred embodiment.

DETAILED DESCRIPTION OF THE PREFERRED EMBODIMENTS

An erection occurs when blood fills two chambers in the penis, known as the corpora cavernosa. This causes the penis to expand and stiffen. The process is triggered by impulses from the brain and genital nerves. Anything that blocks these impulses or restricts blood flow to the penis can result in ED.

Smart Material Based Penile Stimulation Erectile Dysfunction Assistance Device (SMBPSEDAD) which can be used to enhance arousal, measure, stimulate and sustain blood-flow to the penis and genital region, as well as increase sexual pleasure through stimulation. This device is for men who have gone through with difficulty in diagnosing erectile dysfunction, men with periodic episodes and/or sustained periods of erectile dysfunction, as well as men seeking to increase sexual pleasure.

SMBPSEDAD uses "smart material" which contains silicon/shape memory alloy/advanced piezo and/or composites/ macro fiber composites to stimulate blood-flow to the genital region for increased sensation whilst monitoring and measuring blood-flow in real-time. Flexible "smart material" is able to vibrate in an infinite amount of patterns, pulses, and intensities to specifically target various points on the penis for micro-electrical stimulation and blood-flow measurement by sensors, and/or contract and expand, in reaction to blood-flow data being captured and processed.

The device is a low power device, and can be activated by existing/nearby Wi-Fi signals and/or micro-battery. Data collected is wirelessly beamed to cloud data center for processing, or transmitted directly to the users' mobile phone. Processing is handled by software, and customized, actionable data is sent to users' smart-phone for specific wellness and sexual well-being lifestyle tasks to be performed for overall health and sexual performance improvements.

The following device is designed to monitor and aid the erection of a man; it is constructed of a smart material based silicon ring. The original Layered design Proposed by the inventor will enable to include multiple SMA (Smart Material Actuators) within the ring. The optimized design will simulate the pressure points in the penile veins to accelerate the blood flow to the penis.

Based on the sexual performance data measured by the sensors will provide signals for the SMA to contract, allowing the penile veins to accelerate the blood flow and resulting in an erection.

Figure 1:
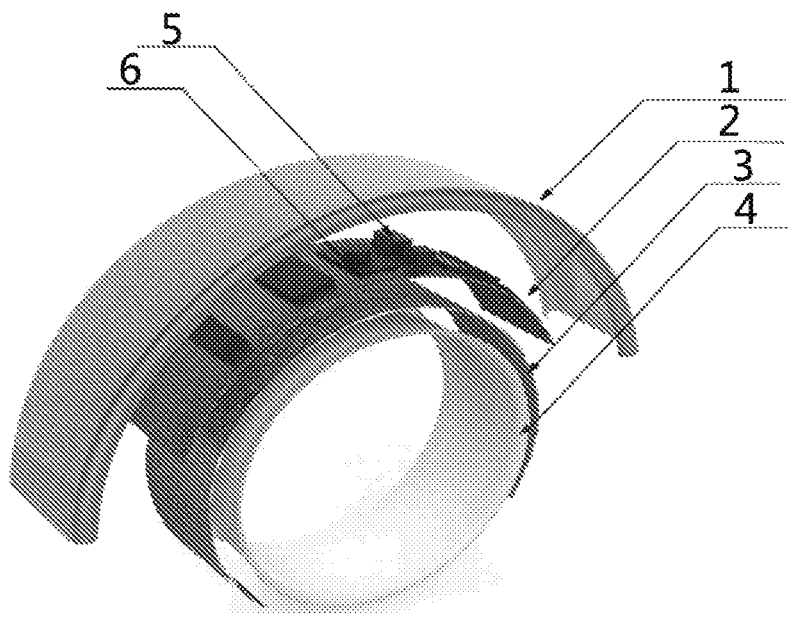
FIG. 1 shows structure of the ring according to the invention.
Figure 2:
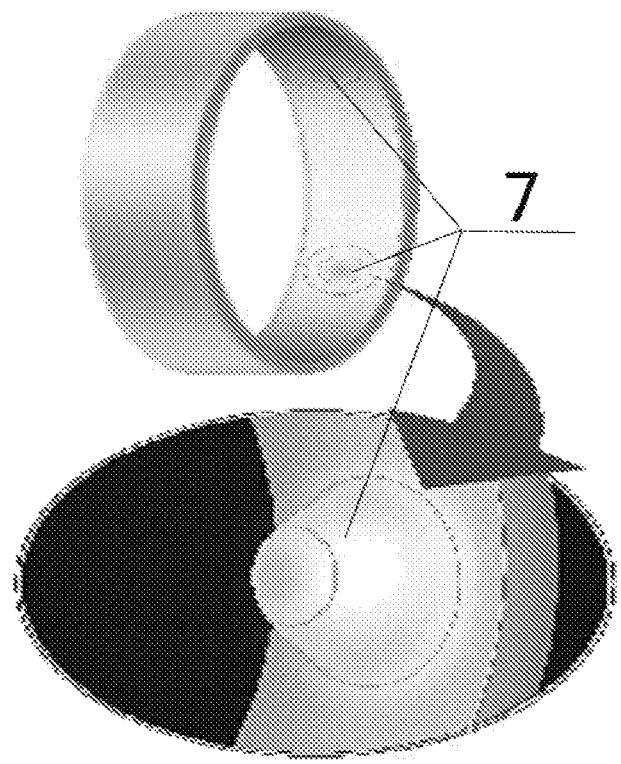
FIG. 2 is an expanded view illustrating the 3D printed structured micro-enhancement modules.

As shown in FIGS. 1-2, Smart Material Based Penile Stimulation Erectile Dysfunction Assistance Device contains measurement sensors that measures circumferential elongation and Doppler blood-flow and blood-flow change;
and power means 5;
and actuation or stimulation part 4;
and data transmission layer 3.

Measurement sensors 6, which are set in the measurement sensor layer 2 to measure temperature. Power means 5 contains Wi-Fi powered/internal flexible battery/internal lithium-ion rechargeable battery/internal lithium-ion disposable battery/internal disposable "coin" battery/liquid ion battery, actuation or stimulation part 4 contains electrical-mechanical stimulation/electrical point 7 stimulation/smart material "contraction" actuation/electrical micro-vibration/ temperature stimulation/texture stimulation. SMBPSEDAD contains data display 1. Data display 1 shows by means of colored lights/LCD display/LED display/flexible-printable display. Data transmits through Bluetooth/NFC/RFID/Wi-Fi/serial. Smart material contains silicon/shape memory alloy/advanced piezo composites/macro fiber composites. SMBPSEDAD is used with or without a condom.

The following table 1 lists the preferable examples to show the structure of the present invention.

TABLE 1

|  | Embodiment A | Embodiment B | Embodiment C | Embodiment D |
| --- | --- | --- | --- | --- |
| measurement sensors layer 2 | temperature blood-flow and blood-flow change | temperature blood-flow and blood-flow change pressure | temperature blood-flow and blood-flow change | temperature blood-flow and blood-flow change |
| power means 5 | internal disposable "coin" battery, liquid ion battery | Wi-Fi powered, internal flexible battery | internal lithium-ion rechargeable battery | internal lithium-ion disposable battery |
| actuation or stimulation part 4 | electrical-mechanical stimulation, electrical point stimulation 7, | electrical micro-vibration or temperature stimulation, texture stimulation | smart material "contraction" actuation, electrical point stimulation 7 | electrical-mechanical stimulation, |
| data transmission layer 3 | Bluetooth | NFC | RFID | Bluetooth |

The ring will collect data from the user during sexual intercourse and/or masturbation and/or sexual stimulation, such as blood-flow to the penis; penis rigidity and sexual arousal. Once the data is collected, the system starts measuring the blood-flow to the penis, and the ring would recognize the flow pattern based on the data model (the sexual well-being matrix, defined per user and software). If the blood-flow becomes too weak to maintain a sufficiently erect and rigid penis for sexual intercourse, the actuators will massage the nerve endings and stimulate more blood to the penis for producing and/or maintaining users' erection.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. Smart material based penile stimulation erectile dysfunction assistance device comprises:
   actuation or stimulation part;
   data transmission layer; and
   measurement sensor layer that measures circumferential elongation and penile blood flow velocity;
   the said actuation or stimulation part, data transmission layer, and measurement sensor layer are set in radial order from an inside to an outside.

2. Smart material based penile stimulation erectile dysfunction assistance device according to claim 1, wherein the said measurement sensor layer having a power means.

3. Smart material based penile stimulation erectile dysfunction assistance device according to claim 2, wherein the said power means comprise internal flexible battery harnessing power from scattered Wi-Fi signals, internal lithium-ion rechargeable battery, internal lithium-ion disposable battery, internal disposable "coin" battery, and/or liquid ion battery.

4. Smart material based penile stimulation erectile dysfunction assistance device according to claim 1, wherein the said measurement sensor layer further comprises a measurement sensor designed to measure micro temperature changes.

5. Smart material based penile stimulation erectile dysfunction assistance device according to claim 1, wherein the said actuation or stimulation part comprises one or more actuation or stimulation modes selected from electro-mechanical stimulation, electrical point stimulation, smart material "contraction" actuation, electrical micro-vibration or temperature stimulation, and/or texture stimulation.

6. Smart material based penile stimulation erectile dysfunction assistance device according to claim 1, further comprising a data display member setting outside or inside of the said device.

7. Smart material based penile stimulation erectile dysfunction assistance device according to claim 6, wherein the said data display member is shown by means of colored lights, LCD display, LED display, and/or flexible-printable display; wherein the said data display member is used to display data in time series chart to let user see his improvement throughout the usage.

8. Smart material based penile stimulation erectile dysfunction assistance device according to claim 1, wherein the said data transmission layer transmits data through Bluetooth, NFC, RFID and/or Wi-Fi.

9. Smart material based penile stimulation erectile dysfunction assistance device according to one of claims 1 to 8, wherein the said actuation or stimulation part, data transmission layer, and/or measurement sensor layer are made of smart material selected from silicon, shape memory alloy, advanced piezo composites, and/or macro fiber composites.

10. Smart material based penile stimulation erectile dysfunction assistance device according to one of claims 1 to 8, which is used in combination with a condom.

11. Smart material based penile stimulation erectile dysfunction assistance device according to claim 1, will use Vibro-tactile stimulation for stimulating the nerves to increase blood flow to the penis.

* * * * *

UNITED STATES PATENT AND TRADEMARK OFFICE
CERTIFICATE OF CORRECTION

PATENT NO. : 10,813,829 B2
APPLICATION NO. : 15/779032
DATED : October 27, 2020
INVENTOR(S) : Biman Najika Liyanage, Mitchell Martin Miller and Alexander Ververis It is certified that error appears in the above-identified patent and that said Letters Patent is hereby corrected as shown below:

On the Title Page

Item (71) Please remove all applicants and list only CIRQ TECHNOLOGIES LIMITED as the applicant.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*